United States Patent
Capote et al.

(10) Patent No.: US 8,979,903 B2
(45) Date of Patent: Mar. 17, 2015

(54) REVISION FIXATION PLATE AND METHOD OF USE

(75) Inventors: Marco Capote, Memphis, TN (US); Robert S. Biscup, Fort Lauderdale, FL (US); Charles L. Branch, Jr., Advance, NC (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1693 days.

(21) Appl. No.: 11/926,407

(22) Filed: Oct. 29, 2007

(65) Prior Publication Data

US 2008/0103502 A1     May 1, 2008

Related U.S. Application Data

(63) Continuation-in-part of application No. 11/411,751, filed on Apr. 26, 2006.

(51) Int. Cl.
*A61B 17/70*     (2006.01)

(52) U.S. Cl.
CPC ......... *A61B 17/7007* (2013.01); *A61B 17/7001* (2013.01)
USPC ............................. 606/258; 606/259; 606/260

(58) Field of Classification Search
CPC ............... A61B 17/70; A61B 17/7007; A61B 17/7008; A61B 17/80; A61B 17/8023; A61B 17/8033; A61B 17/8047
USPC ............. 606/250, 258–260, 70, 71, 271, 273, 606/274
See application file for complete search history.

(56) References Cited

U.S. PATENT DOCUMENTS

| | | | |
|---|---|---|---|
| 4,836,196 A | 6/1989 | Park | |
| 5,540,688 A | 7/1996 | Navas | |
| 5,984,924 A | 11/1999 | Asher et al. | |
| 6,520,963 B1 * | 2/2003 | McKinley | 606/266 |
| 6,682,532 B2 | 1/2004 | Johnson et al. | |
| 2003/0100904 A1 | 5/2003 | Biedermann | |
| 2005/0143737 A1 | 6/2005 | Pafford et al. | |

FOREIGN PATENT DOCUMENTS

| | | | | |
|---|---|---|---|---|
| FR | 2697428 A | 6/1994 | | |
| FR | 2846223 A | 4/2004 | | |
| WO | WO 03/043511 A1 * | 5/2003 | ............. | A61B 17/70 |

* cited by examiner

*Primary Examiner* — Eduardo C Robert
*Assistant Examiner* — Julianna N Harvey

(57) ABSTRACT

A connection system is provided that joins a revision fixation plate to a previously implanted skeletal fixation plate. In one form, the system allows the previously implanted plating system to be revised without disturbing the original implant components. In one aspect, the connection includes joining the revision fixation plate to a previously implanted fastener. In another aspect, the revision fixation plate is directly joined to a previously implanted fixation plate. In yet another aspect, the connection includes forming a dynamic relationship between the previously implanted plating system, the revision fixation plate, and the affected vertebrae. In one form, the dynamic relationship enables movement between the previously implanted plating system and the affected vertebrae and in another form, the dynamic relationship enables movement between the previously implanted plating system and the revision fixation plate.

14 Claims, 11 Drawing Sheets

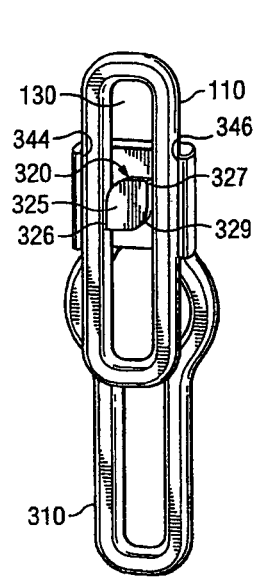 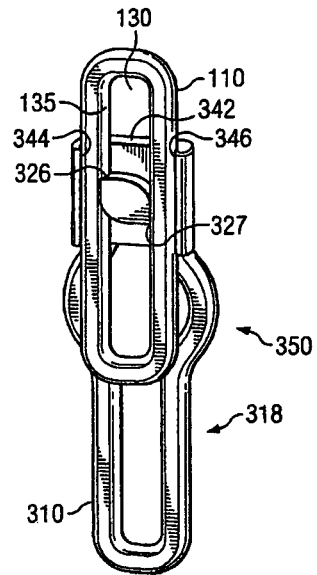
*Fig. 3B*   *Fig. 3C*
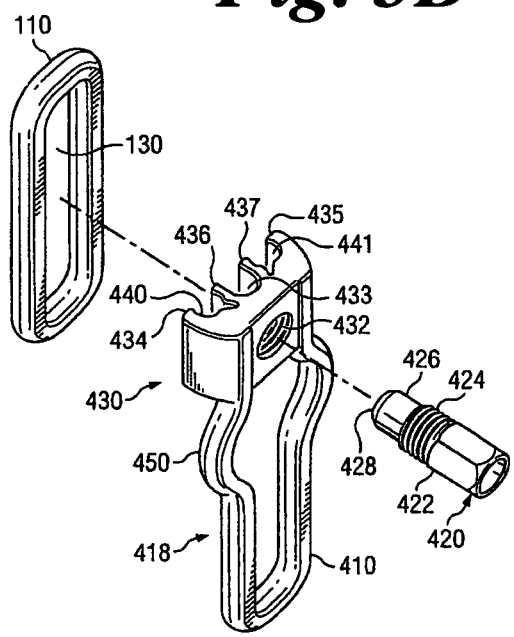 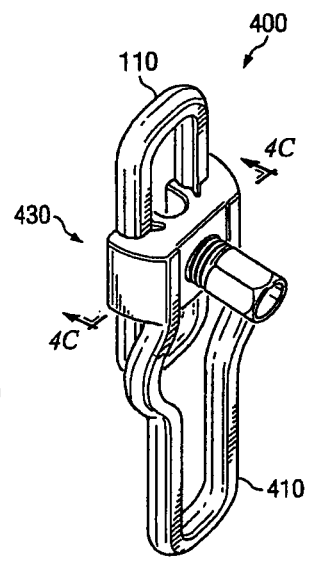
*Fig. 4A*   *Fig. 4B*

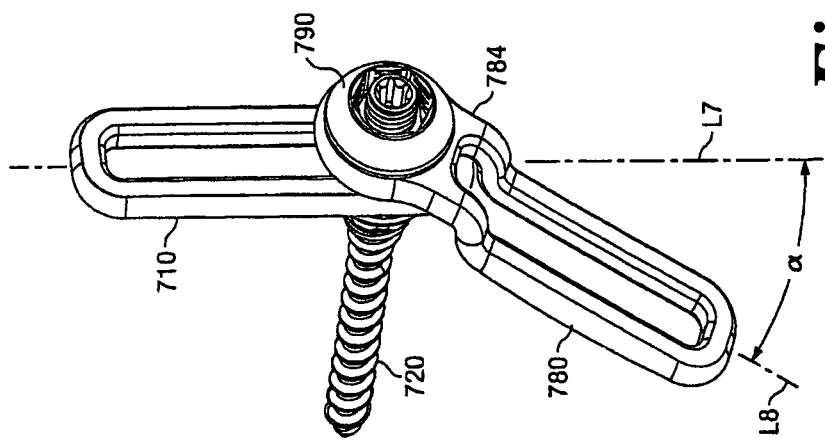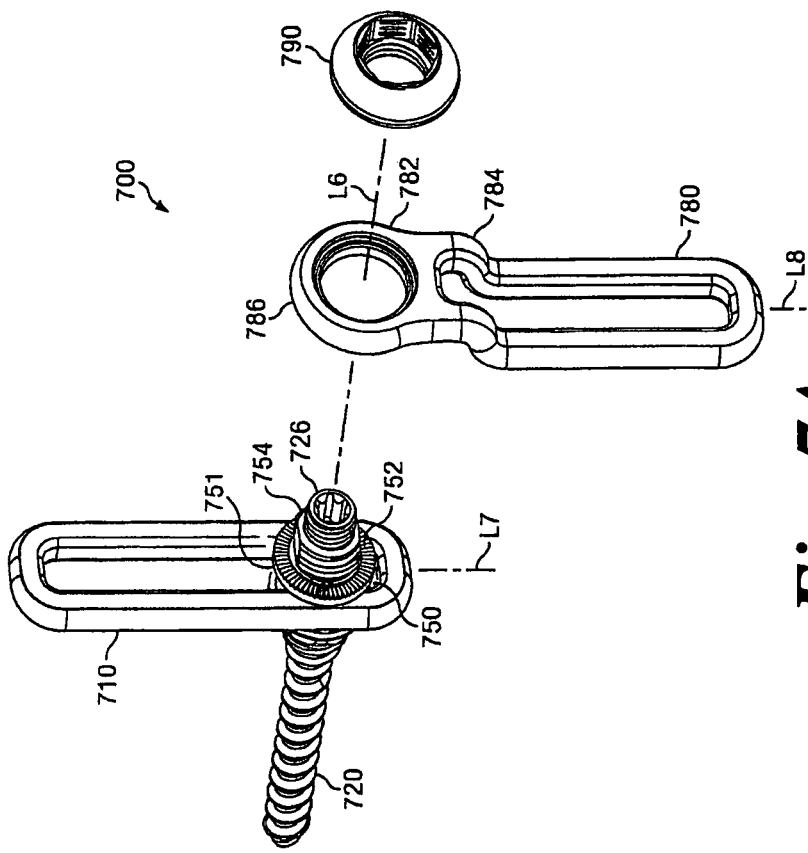

REVISION FIXATION PLATE AND METHOD OF USE

This application is a Continuation-In-Part of U.S. patent application Ser. No. 11/411,751 filed Apr. 26, 2006, which is hereby incorporated by reference.

The present application relates generally to a fixation system for the treatment of the skeletal system. More particularly, the present invention may be applied to treatment of the human spine.

Spinal fusion is performed to prevent motion between mobile segments of the spine. A variety of reasons exist for performing spinal fusion. The spine may be unstable due to a traumatic injury, surgery, or invasion and destruction of the vertebrae by tumor. Continued motion of particular segments of the spine may cause overgrowth of joint and ligamentous tissue which, in turn, may compress the spinal cord or its nerves. The curvature of the spine may become abnormal and cause deformity or neurological problems. In these instances, it may be desirable to prevent spinal motion at the affected levels.

The spine is composed of individual bones, or vertebrae, stacked on top of each other in a column. Each vertebra includes a cylindrical vertebral body, which participates in weight bearing, and an arch of bone (comprising the lamina and spinous process) which protects the spinal cord and its coverings. The bony arch is connected to the vertebral body by two small columns of bone, referred to as the pedicles. The circular canal between the body, the arch, and the pedicles houses the spinal cord and is called the spinal canal. Between adjacent vertebral bodies lie the intervertebral discs. These are cartilaginous structures that function as shock absorbers for the spine. Facet joints connect the bony arches of the spine and permit spinal motion between adjacent vertebrae.

Spinal instrumentation is employed as an adjunct to successful spinal fusion. The instrumentation immobilizes the spine while the body forms new, solid bone. Spinal fusion usually is performed by surgically exposing the area of the spine to be fused and thereafter preparing the exposed bone by removing soft tissue and ligaments so new bone can form over the area. After the surgical site has been prepared, an autogenic bone graft (from another part of the body, usually the hip) or an allogenic bone graft (from a cadaver) can be implanted in the prepared area so that new bone can form around and within the implant. Implants have been developed in an attempt to avoid the problems associated with acquiring a bone graft implant. Regardless of the type of implant that is used, the chances of achieving a successful fusion are enhanced if motion in the area is minimized or prevented while new bone forms. Further, even when an initial fusion surgery is successful, adjacent spine levels may be become affected and need instrumentation to promote a fusion at the adjacent level. In such a situation, it is desirable to revise the initial surgical procedure.

Although there have been advances in this area, there remains a need for improved stabilization systems for use in skeletal fixation and bony fusion procedures.

SUMMARY OF THE INVENTION

The present application relates generally to fixation of the skeletal system.

In one embodiment, a system is provided for extending a first implanted spinal fixation element to one or more adjacent vertebrae. In one aspect, the system includes an elongated extension member having at least one locking projection for engaging the first implanted spinal system to inhibit rotation between the two components.

In yet a further aspect, the present invention provides a spinal fixation system for joining a first vertebra to a second vertebra. The fixation system comprising an elongated fixation member, a first bone anchor, a second bone anchor and at least one coupler for joining one of the first bone anchor or second bone anchor to the fixation member, wherein the coupler receives the bone anchor in an internal passage and has an outer threaded surface.

In another embodiment, the present invention provides a method for revising a first implanted spinal fixation system attached to the spine with at least one bone anchor and a dual action coupling element. The method includes providing an extension member and a locking member, positioning one end of the extension member adjacent the dual action coupling element and locking the locking member to the dual action coupling element such that the dual action coupling element participates in locking the first implanted spinal fixation system to the spine and locking the extension member to the first implanted spinal fixation system.

In another aspect, a system is provided for extending a first, implanted spinal fixation element to one or more adjacent vertebrae while leaving the first, implanted spinal fixation element in place. A flexible elongated extension member extends from the implanted spinal fixation element to at least one additional vertebra.

In another embodiment, a system is provided for extending a first, implanted spinal fixation element to one or more adjacent vertebrae. The system includes a first flexible coupler and a second flexible coupler positioned at a coupling end portion of an elongated extension member.

There is also disclosed a system for extending a first, implanted spinal fixation element to one or more additional adjacent vertebrae while leaving the first, implanted spinal fixation element in place, which includes a flexible elongated extension member having a longitudinal axis extending between a coupling end portion and a bone engagement end portion. The flexible elongated extension member may have a length between the coupling end portion and the bone engagement portion to extend from said first, implanted spinal fixation element to at least one additional vertebra. A first fastener to position said coupling end portion on the first, implanted spinal fixation element, and a second fastener locking the coupling end portion to the first fastener are also provided. The elongated extension member can be made of plastic, such as polyetheretherketone or polyketone. The flexible elongated extension member can be configured to provide a dynamic relationship between the first, implanted spinal fixation element and the additional vertebra(e). A washer can be provided configured to position the coupling end portion on the first, implanted spinal fixation element.

A system for extending a first, implanted spinal fixation element having a bone fastener attached to one or more additional vertebrae while leaving the bone fastener in place could include an elongated extension member having a longitudinal axis extending between a coupling end portion and a bone engagement end portion, the elongated extension member having a length between the coupling end portion and the bone engagement portion to extend from the first, implanted spinal fixation element to at least one additional vertebra. A first fastener to position the coupling end portion on the first, implanted spinal fixation element is included, as well as a first flexible coupler positioned between the first, implanted spinal fixation element and the bone fastener and a second flexible coupler positioned between the coupling end portion and the first, implanted spinal fixation element. Either or both flexible couplers may be made of silicone or plastic, and the first fastener can be a dual threaded nut. In one embodiment, the first and second flexible couplers are configured to provide a dynamic relationship between the first, implanted spinal fixation element and the vertebra(e), and/or a dynamic relationship between the first, implanted spinal fixation element and the elongated extension member.

Methods are also disclosed, which may include providing a flexible elongated extension member having a longitudinal axis extending between a coupling end portion and a bone engagement end portion and having a length between the coupling end portion and the bone engagement portion to extend from a first, implanted spinal fixation system to at least one additional vertebra; accessing the first implanted spinal fixation system in a medical patient; implanting the coupling end portion of the extension member on the first, implanted spinal fixation system; implanting the bone engagement end portion on the one or more additional adjacent vertebrae; and attaching the coupling end portion to the first, implanted spinal fixation system to provide a dynamic relationship between the extension member and the first, implanted spinal fixation system. Such methods may also include attaching the bone engagement end portion to the one or more additional adjacent vertebrae to join the extension member to the one or more additional adjacent vertebrae.

Other methods may include providing an elongated extension member having a longitudinal axis extending between a coupling end portion and a bone engagement end portion and having a length between said coupling end portion and the bone engagement portion to extend from a first, implanted spinal fixation system to at least one additional vertebra; accessing the first, implanted spinal fixation system in a medical patient; implanting a first flexible coupler on the first, implanted spinal fixation system; implanting the coupling end portion of the extension member on the first flexible coupler; implanting a second flexible coupler on the coupling end portion; and attaching the coupling end portion to the first, implanted spinal fixation system to provide movement between the extension member and the first, implanted spinal fixation system. Such methods can also include implanting the bone engagement end portion on the one or more additional adjacent vertebrae, and/or attaching the bone engagement end portion to the one or more additional adjacent vertebrae to join the extension member to the one or more additional adjacent vertebrae. One can also sandwich the coupling end portion of the extension member between the first flexible coupler and the second flexible coupler.

Further aspects, forms, embodiments, objects, features, benefits, and advantages of the present invention shall become apparent from the detailed drawings and descriptions provided herein.

BRIEF DESCRIPTION OF THE DRAWINGS

FIG. 3B is a perspective view of an assembled combination of the components of FIG. 3A in an unlocked condition.

FIG. 3C is a perspective view of an assembled combination of the components of FIG. 3A in a locked condition.

FIG. 4A is a partially exploded perspective view of an implanted system and a further embodiment of a revision system according to another aspect of the present invention.

FIG. 4B is a perspective view of an assembled combination of the components of FIG. 4A.

FIG. 7A is a partially exploded perspective view of a fixation system according to another aspect of the present invention.

FIG. 7B is an assembled perspective view of the fixation system of FIG. 7A.

DETAILED DESCRIPTION OF THE ILLUSTRATED EMBODIMENTS

Figure 1:
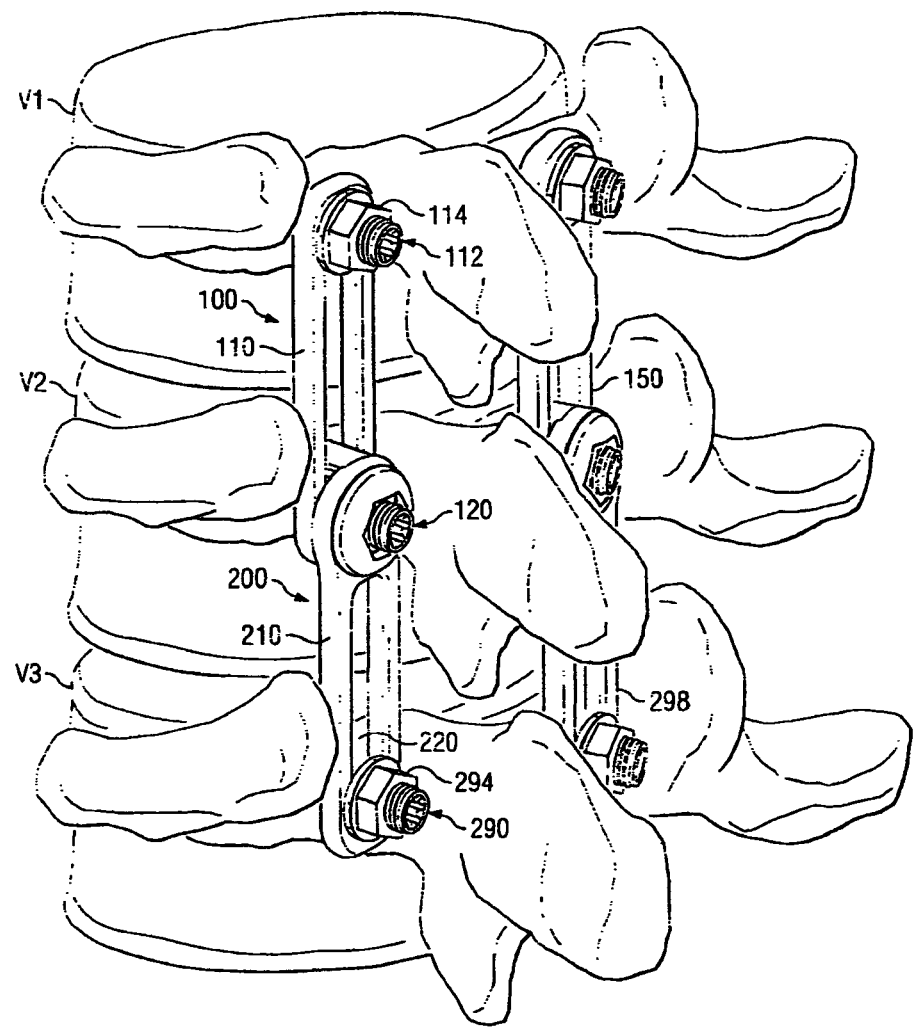
FIG. 1 is a perspective view of a revision system according to one aspect of the present invention implanted in the spine.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein, are contemplated as would normally occur to one skilled in the art to which the invention relates.

Spinal fixation systems, such as rod/screw systems and plate/screw systems, are often used to at least partially stabilize the spine to reduce movement between adjacent vertebrae. In some patients, there is a need to address continued degradation of the spine near the previously implanted spinal fixation system. In these circumstances, it is desirable to have a revision fixation system that may be added onto the previously implanted fixation system to extend the composite system to one or more nearby spinal levels.

Figure 2A:
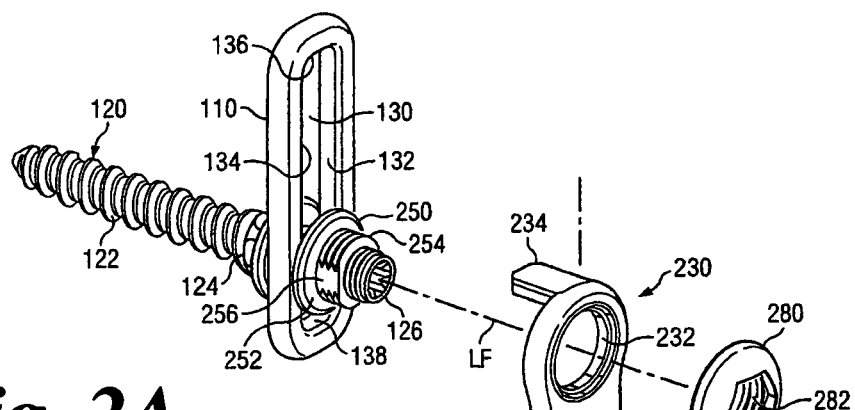
FIG. 2A is a partially exploded perspective view of an implanted system and a revision system according to one aspect of the present invention.
Figure 2B:
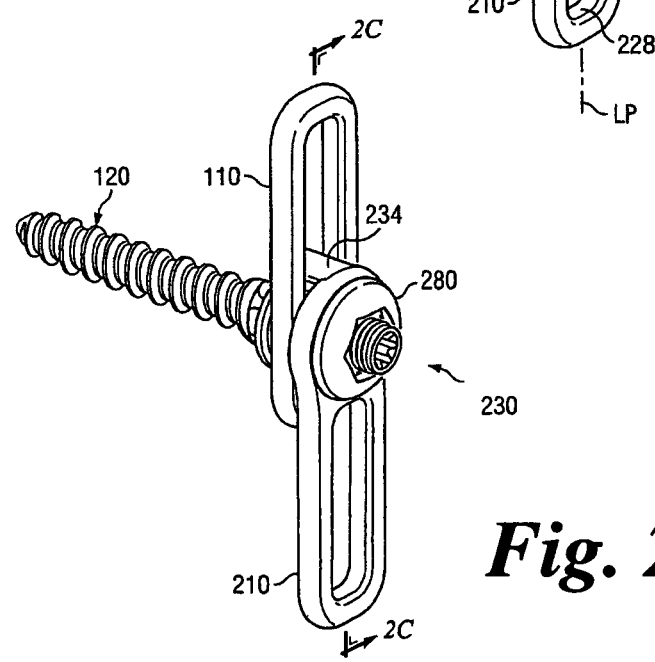
FIG. 2B is a perspective view of an assembled combination of the components of FIG. 1.
Figure 2C:
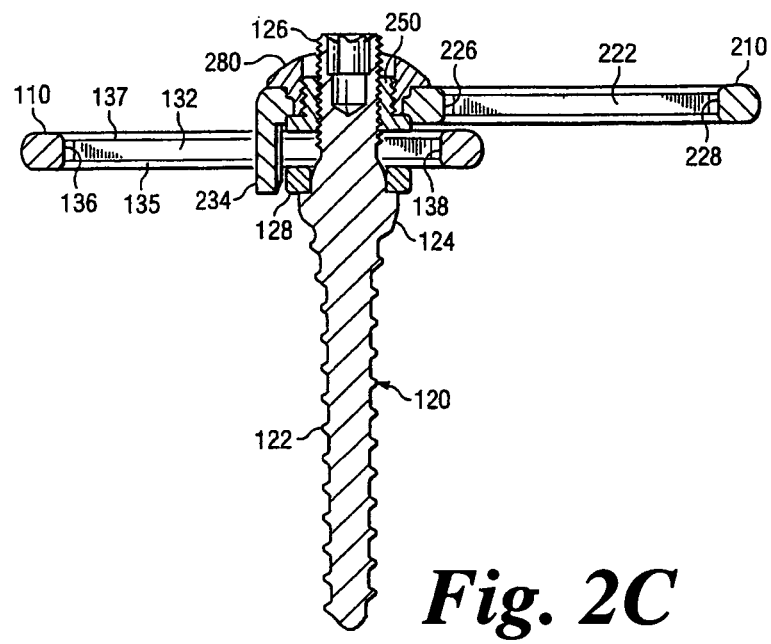
FIG. 2C is a partial cross-sectional view taken along line 2C-2C of FIG. 2B.

Referring now to FIGS. 1-2C, there is shown an embodiment of a revision fixation plate system 200 in combination with a previously implanted spinal fixation system 100. The previously implanted fixation system 100 includes a plate 110 extending between vertebrae V1 and V2 having an internal slot 130. A bolt 120 extends through slot 130 into the pedicle of vertebra V2 and is initially coupled to the plate 110 by an internally threaded nut similar to nut 114. In a similar manner, a bolt 112, similar to bolt 120, extends through slot 130 into the pedicle of the vertebrae V1 and is coupled to the plate 110 by internally threaded nut 114. Bone bolt 120 includes a bone engaging threaded shaft 122, an enlarged seat area 124 and an externally threaded coupling shaft 126 having machine threads to receive a fastener such as nut 114. In the illustrated embodiment, disposed between seat 124 and plate 110 is an enlarged washer 128 adapted to engage the underside of the plate. In the illustrated embodiment, the bone bolt 120 has an external drive pattern on the enlarged seat 124 and an internal hex drive pattern formed adjacent externally threaded coupling shaft 126. The slot 130 in the plate 110 is defined by opposing elongated side walls 132, 134 and opposing end walls 136, 138. The top of the walls forming the slot 130 is chamfered or rounded to form surface 137 and the bottom of the walls are also chamfered to form surface 135. In the embodiment illustrated in FIG. 1, there is a second previously implanted spinal fixation system 150 extending between V1 and V2 on the opposite side of the spinous processes.

In the illustrated embodiment, the revision fixation plate system 200 is shown in combination with the previously implanted fixation system 100. The fixation plate system includes an extension plate 210 having a fixation portion 218 with a slot 220 defined by opposed elongated side walls 222, 224 and end walls 226, 228. The extension plate 210 also includes a connection portion 230 adapted for coupling to a previously implanted fixation system. Connection portion 230 includes a substantially cylindrical aperture 232 and a projecting flange 234 extending along axis LF transverse to the longitudinal axis LP of the plate. Projecting flange 234 has a width that substantially matches the width of the slot 130 and/or the length of the end walls 136, 138 to lock the extension plate 210 to the plate 110 to inhibit rotation therebetween. Further, as shown in FIG. 2C, the projection has a length transverse to the longitudinal axis of the plate 210 that is greater than the thickness from the top coupling surface to the bottom bone engaging surface of the plate 110.

The revision fixation plate system 200 further includes a coupling member 250 and a cooperating internally threaded nut 280 to join the extension plate 210 to the plate 110. Coupling member 250 has an enlarged flange 252 having a diameter larger than the width of slot 130 such that the flange engages plate 110. Coupling member 250 has an internally threaded bore configured to threadedly engage externally threaded shaft 126 of the bone bolt 120 and an external drive surface 256 and an opposing drive surface (not shown). The drive surface 256 allows a tool to engage the coupling member 250 and advance it along threaded shaft 126. The exterior of the coupling member 250 has a series of external threads 254 interrupted by the drive surface 256. Threaded nut 280 includes an internally threaded aperture 282 and an internal drive socket 284. The internally threaded aperture 282 is configured for threaded engagement with the external threads 254 of the coupling member.

In the assembled configuration shown in FIGS. 2B and 2C, the extension plate 210 is positioned in substantial longitudinal alignment with the previously implanted fixation plate 110. The previously installed coupling member 250 and projecting portion of threaded shaft 126 are received within aperture 232 at the connection portion of the plate. Aperture 232 has a stepped lower surface as best seen in FIG. 2C sized to matingly receive the flange 252. With the coupling member positioned in aperture 232, projecting flange 234 extends into and through slot 130 to lock the alignment of plate 210 with the alignment of plate 110. Projecting flange 234 is sized to substantially mate with the walls of the slot 130 to prevent rotation between plate 110 and plate 210. Locking nut 280 is threadedly advanced along the exterior threads 254 such that the nut engages connection portion 230 of plate 210. As shown in FIG. 2C, the enlarged shoulder on the underside of nut 280 mates with a corresponding annular ring formed in the upper portion of aperture 232. In one aspect, the extension plate 210 directly engages the previously implanted fixation member 118 and is spaced by the coupling member flange 252 from direct contact with previously implanted plate 110. It will be appreciated that the extension plate 210 may be positioned at a plurality of locations with respect to plate 110 since it engages the bone bolt 120.

In use, the surgeon identifies the location of the previously implanted fixation systems 100, 150. An evaluation, generally through non-invasive imaging, is performed to determine the length of revision system needed to address the additional spinal segment(s) needing fixation. Once the initial evaluation is complete, the surgeon gains surgical access to the site within the patient and performs any decompression, fusion or other necessary procedure on the patient. If a coupling member 250 was utilized during the initial installation, then the previously implanted fixation system is ready for extension. If a conventional fastener such as nut 114 was utilized on bone fastener 120, then the conventional fastener is removed. A coupling member 250 according to the present invention is then placed on the threaded coupling shaft 126 and advanced along the threads by a tool (not shown) engaging drive surface 256 to lock plate 110 to the bone bolt 120. If necessary, a secondary tool may engage the internal drive socket of bone bolt 120 to prevent rotation of the bone screw portion within the bone of the patient. After the coupling member 250 is installed, connection portion 230 is positioned over the coupling member 250 and advanced toward the patient such that the coupling member 250 extends into aperture 232 and locking projection 234 extends into slot 130 of the previously implanted plate 110. Once the extension plate 210 is properly positioned, locking nut 280 is advanced on external threads by a tool (not shown) engaging the internal drive socket 284 of the locking nut. The extension plate 210 extends to at least vertebra V3 such that fixation portion 218 is positioned adjacent the bone. A bone fixation member 290 similar to bolt 120 is inserted through slot 220 and a nut 294 is applied to lock the extension plate 210 to vertebra V3. In a similar manner, companion extension system 298 is attached to a previously implanted fixation system 150.

In the illustrated embodiment, the longitudinal axis of the plate 110 is in substantial alignment with the longitudinal axis LP of plate 210. However, it is contemplated that in an alternative embodiment, the projection 234 may be positioned off the longitudinal axis LP of plate 210 such that the alignment of the extension plate 210 does not have to correspond to the alignment of the previously implanted plate.

Figure 3A:
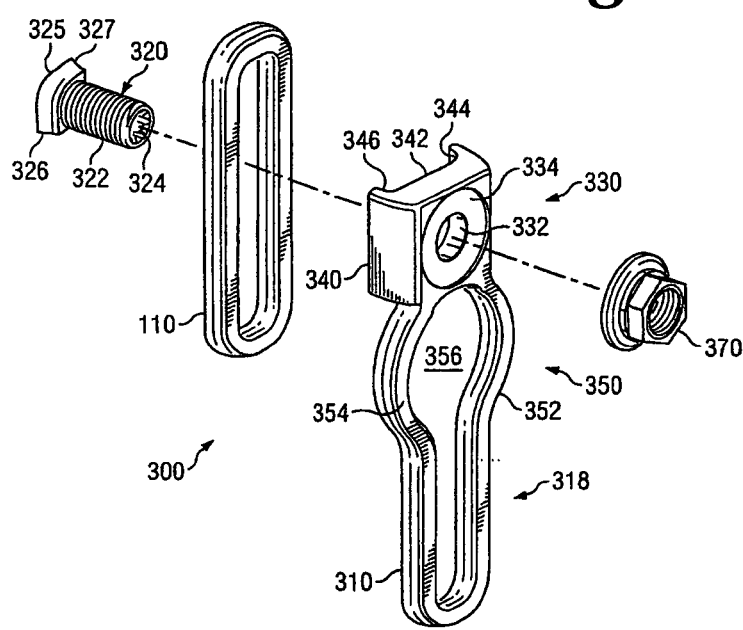
FIG. 3A is a partially exploded perspective view of an implanted system and a further embodiment of a revision system according to another aspect of the present invention.

Referring now to FIGS. 3A-3C, there is shown a further embodiment of an extension system according to the present invention. Illustration of plate 110 is provided as an indication of a previously implanted fixation system 100 as shown in FIG. 1. Further description of the implanted fixation system 100 will not be described except as necessary to understand the application of the extension system to the existing system. Extension system 300 includes a plate 310, a coupling member 320, and a locking member 370. The plate 310 includes a fastening portion 318 for joining to the bone adjacent to the fixation system 100 and a coupling portion 330 for joining to the previously implanted fixation system 100. Unlike the embodiment described with respect to FIGS. 1-2C, the present embodiment is intended to join directly to the plate 110 and bypass the previously implanted bone fastener. Thus, the plate 310 is provided with an enlarged bone fastener bypass portion 350 disposed between the coupling portion 330 and the bone fastening portion 318. The bypass portion 350 in the slotted portion of plate 310 is bound by opposing arcuate side walls 352 and 354 defining substantially cylindrical aperture 356.

The coupling member 320 includes an enlarged head 325 and a threaded shaft 322. The enlarged head 325 includes a pair of opposing extensions 326 and 327. When the extensions are oriented in a first position as shown in FIG. 3B, the head 325 is sized to pass through the slot in plate 110. When oriented in a second position as shown in FIG. 3C substantially 90 degrees rotation from the first position, the extensions 326 and 327 engage the lower surface of the plate 110 such that the coupling member head cannot pass through the slot in the plate 110. An internal socket 324 is provided in the threaded shaft such that a tool may be used to orient the head 325 and maintain the desired position as locking member 370 is tightened.

The connection portion 330 of the extension system 300 includes a substantially solid block 340 defining a central aperture 332 with a surrounding annular recess 334. The block 340 further defines a pair of flanges 344, 346 projecting from block 340 transverse to the longitudinal axis of the plate to define a channel 342 on the bottom surface. The channel 342 is configured and sized to receive the plate 110. In the illustrated embodiment, the channel 342 is in substantial alignment with the longitudinal axis of the plate 310.

It is contemplated that the extension system 300 will be implanted as an extension of a previously implanted fixation system 100 as shown in FIG. 1. In use, the surgeon will gain surgical access to the previously implanted system. The enlarged head of the coupling member 320 will be passed through the slot in the plate 110. The plate 310 will be aligned with the plate 110 such that the bypass portion 350 is positioned over the previous implanted bone fastener device, if one exists. The threaded post 322 will be aligned with the opening 332 and the plate 310 advanced into engagement with plate 110. The flanges 344 and 346 will be positioned on either side of the previously implanted plate and the locking nut 370 will be threaded onto threaded post 322 to lock the extension plate firmly to the previously implanted fixation system. At least one bone fastener is used to join the plate 310 to the bone.

Figure 4C:
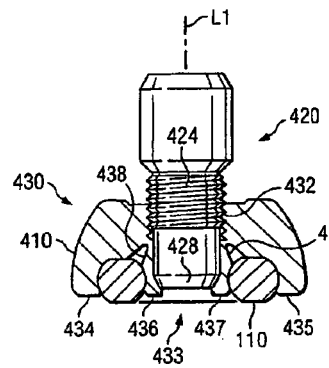
FIG. 4C is a partial cross-sectional view taken along line 4C-4C of FIG. 4B.

Referring now to FIGS. 4A-4C, there is shown a further embodiment of an extension system according to the present invention. Extension system 400 includes a bone fastening portion 418, a fastener bypass portion 450, and a connection portion 430. Connection portion 430 includes an internally threaded aperture 432 extending transverse to the longitudinal axis of the plate and opening into a passage 433. The connection portion 430 has a width greater than the width of plate 110 and includes a pair of external flanges 434, 435 extending substantially transverse to the longitudinal axis of the plate with an internal distance between the flanges sufficient to receive at least a portion of plate 110. A pair of internal flanges 436, 437 extend substantially parallel to external flanges 434, 435 to define plate receiving channels 440 and 441 therebetween, respectively. Plate receiving channels 440, 441 define notches 438, 439 as shown in FIG. 4C. In one form, notches 438, 439 are configured to contribute to the flexibility of internal flanges 436, 437. Internal flanges 436, 437 define passage 433 therebetween. As best seen in FIG. 4C, each of internal flanges 436, 437 have a reduced width portion adjacent their connection to a plate body 410 and a sloped bearing surface adjacent passage 433 tapering to narrow the passage towards the bottom of the connection portion 430. As a result of the reduced width portion, internal flanges 436, 437 may flex inward to allow loading of the plate into channels 440, 441 and outwardly to lock the plate in position. External flanges 434, 435 each have an inner surface with a lower edge. The lower edge of the inner surface extends inwardly slightly to form a concave recess to receive a portion of the plate and cooperate in locking the plate 110 to the connection portion 430.

A locking member 420 is formed substantially as a set screw with an external driving portion 422 and an external thread form 424. A projecting cylindrical shaft 426 extends beyond thread form 424 and terminates in conical portion 428. It is contemplated that locking member 420 is a break-off set screw such that after tightening the driving portion 422 may be sheared off to lower the profile of the extension system 400.

Use of the extension system 400 is substantially the same as previously described above with respect to system 300. However, unlike system 300, extension system 400 is attached to the previously implanted fixation system 100 without any components engaging the bottom of the plate 110. Specifically, the connection portion 430 is aligned with the plate 110 with a bypass portion 450 positioned adjacent any previously implanted bone fixation devices. The connection portion 430 is press fit onto the plate 110 with each side portion of the plate received in channels 440 and 441. As explained above, the internal flanges 436 and 437 flex inward slightly to allow the plate to be seated in the channels. Locking member 420 is threadedly advanced into passage 433 along axis L1 to force conical surface 428 against the bearing surfaces of the internal flanges. Continued advancement of the conical portion 428 against the bearing surfaces forces the internal flanges 436, 437 toward the external flanges 434, 435 thereby capturing the plate 110 within the channels 440 and 441. In an alternative embodiment, the internal flanges 436, 437 are preformed to allow the plate 110 to be positioned within the channels 440 and 441 and are moved thereafter to lock the plate in the channels 440 and 441.

Figure 5A:
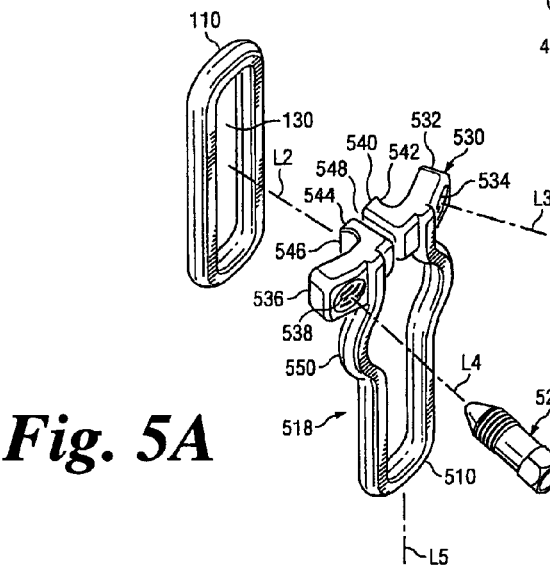
FIG. 5A is a partially exploded perspective view of an implanted system and a further embodiment of a revision system according to another aspect of the present invention.
Figure 5B:
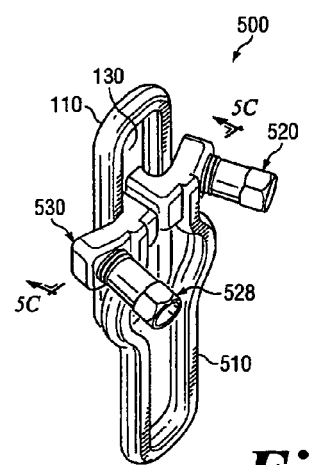
FIG. 5B is a perspective view of an assembled combination of the components of FIG. 5A.
Figure 5C:
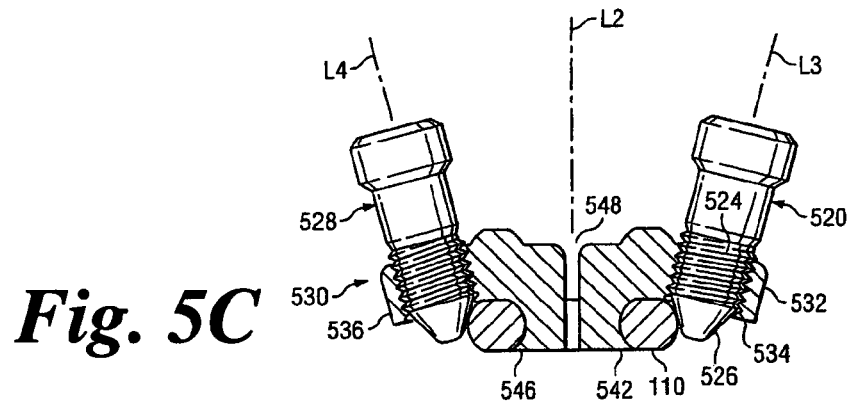
FIG. 5C is a partial cross-sectional view taken along line 5C-5C of FIG. 5B.

Referring now to FIGS. 5A-5C, there is shown a further embodiment of an extension system in accordance with another aspect of the present invention. Extension system 500 includes an elongated plate 510 having a bone fastener portion 518, a connection portion 530, and a fastener bypass portion 550. Connection portion 530 includes a first lateral extension 532 extending laterally away from longitudinal axis L5. An internally threaded bore 534 is formed in lateral extension 532 extending along axis L3. In a similar manner, a second lateral extension 536 has an internally threaded bore 538 extending along axis L4. The connection portion 530 is divided into independent halves by a gap 548. First lateral extension 532 also includes an internal flange 540 projecting transverse from the longitudinal axis toward the previously implanted fixation system 100. Internal flange 540 includes an external side wall having a concave recessed area terminating in a tip 542 projecting laterally. Similarly, second lateral extension 536 also includes an internal flange 544 projecting transverse from the longitudinal axis toward the previously implanted fixation system 100. Internal flange 544 includes an external side wall having a concave recessed area terminating in a tip 546 projecting laterally.

The extension system 500 is used to extend a previously implanted system 100 as described above. In operation, the user positions the extension system 500 in alignment with a portion of plate 110 such that bypass portion 550 is aligned with a preexisting bone fixation member, if it is necessary to straddle the bone fixation member to have sufficient area to complete the connection. Either manually or with a tool, the sides of the plate 510 may be compressed to narrow the gap 548 such that the tips 542 and 546 move medially. In this compressed form, the tips may pass through the slot 130 of the plate 110 as plate 510 is advanced along axis L2 into engagement. Once the internal flanges are positioned in the slot 130, locking members 520 and 528 may be applied. Locking member 520 has a driving portion 522, an externally threaded shaft 524, and a conical tip 526. Locking member 528 is similarly formed. As best seen in FIG. 5C, locking member 520 is advanced with threaded opening 534 along axis L3. In the illustrated embodiment, axis L3 extends at an oblique angle with respect to axis L2. Continued advancement of the set screw locking member 520 along axis L3 forces conical tip 526 against plate 110 thereby forcing the plate member medially into locking engagement with internal flange 540 and the projecting tip 542. In a similar manner, locking member 528 is advanced along axis L4, extending non parallel to axis L2, within bore 538. As the locking member advances, the tip engages the opposite side of plate 110 and forces it medially toward internal flange 544 and projection 546, thereby locking the connection assembly 530 and plate 110. If necessary, removal may be accomplished by reversing the connection members to allow movement of the plate 110 with respect to the internal flanges.

Figure 6A:
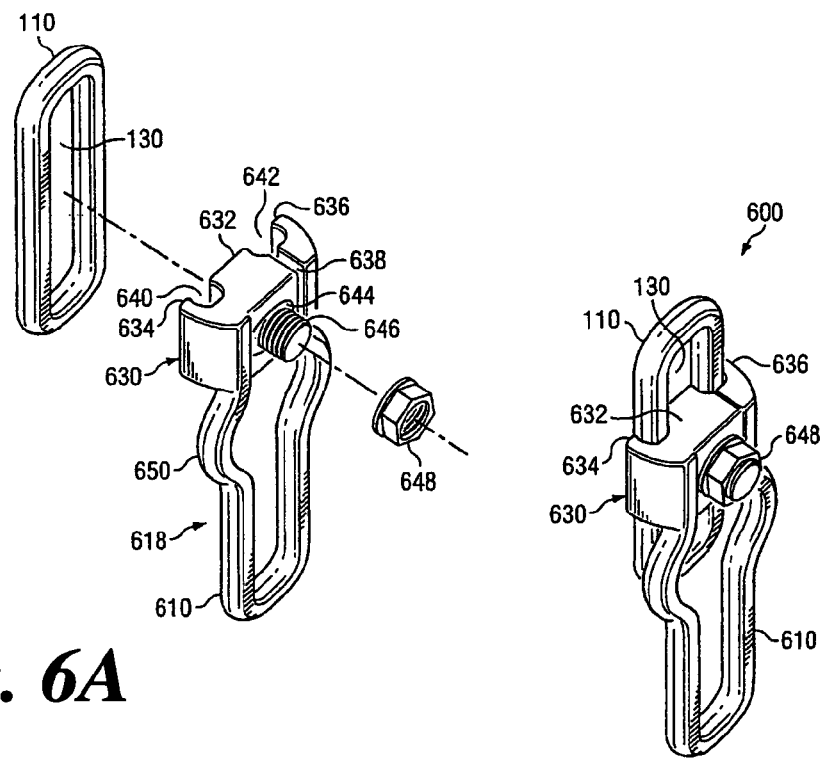
FIG. 6A is a partially exploded perspective view of an implanted system and a further embodiment of a revision system according to another aspect of the present invention.
Figure 6B:
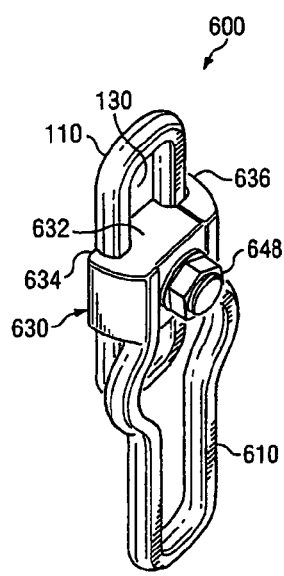
FIG. 6B is a perspective view of an assembled combination of the components of FIG. 6A.

Referring now to FIGS. 6A and 6B, there is shown a further embodiment of an extension assembly according to the present invention. Extension assembly 600 includes a slotted plate 610 having a bone fastener area 618, a fastener bypass area 650, and a coupling portion 630. The coupling portion 630 includes a first lateral flange 634 extending substantially transverse to the longitudinal axis of the plate 610 and a second lateral flange 636 extending substantially transverse to the longitudinal axis of the plate 610, the first and second lateral flanges 634 and 636 having medial facing surfaces spaced from each other a distance greater than the width of the plate 110 at the connection area. A central internal flange 632 projects downward toward the previously implanted fixation plate and the underlying bone. A first channel 640 is defined between lateral flange 634 and central flange 632. Similarly, a second channel 642 is defined between lateral flange 636 and central flange 632. Second flange 636 includes a projecting arm 638 that is received within a passage of coupling portion 630 and has an end that ends into channel 640. A coupling member 646 extends through an aperture 644 and engages the projecting arm 638. A locking nut 648 is threaded onto threads of the coupling member to lock the projection arm 638 in relative position in comparison to the lateral flange 634.

In use, the coupling portion is positioned over plate 110 such that the plate sides extend within channels 640 and 642 as shown in FIG. 6A. Either by manual force or with a compression tool, the second lateral flange 636 is urged toward the first lateral flange 634 thereby closing channels 640 and 642. Thus, the lateral flanges with the inwardly projecting tips at their distal end lockingly hold the plate 110 from translational and rotational movement. Locking nut 648 is threaded onto the post 646 to maintain the lateral flanges in the locking position shown in FIG. 6B.

Referring now to FIGS. 7A and 7B, there is shown still a further embodiment of a fixation system 700 according to another aspect of the present invention. Plate 710 represents a previously implanted fixation system attached to the bone via a bone screw 720 having a post 726 with a series of external machine threads. The plate 710 extends along longitudinal axis L7 with an upper surface extending substantially along an implant plane and the bone screw 720 extends along axis L6 extending substantially transverse to axis L7. A dual threaded coupling nut 750 is applied to and threadedly engaged with post 726 to couple plate 710 to bone screw 720. Nut 750 includes a plurality of splines 752 radially extending along the surface of a washer flange 751 adjacent to an externally threaded post 754. In the illustrated embodiment, the washer flange 751 is integrally formed with the threaded post 754 of nut 750.

An elongated extension member 780 is provided extending along longitudinal axis L8. In the illustrated embodiment, the extension member 780 is a slotted plate having an upper surface extending substantially along a first plane formed with a connection portion 782 extending substantially along a second plane. Extending between the slotted plate portion and the connection portion 782 is profile reduction transition area 784 sloping between the first plane and the second plane. Defined on the bottom of the connection portion 782 is a series of radially extending splines 786 substantially identical to splines 752 in size and arrangement such that they may mate with splines 752. It will be appreciated that extension member 780 may be positioned at a plurality of angular relations with respect to plate 710 such that longitudinal axis L8 may extend at an angle "α" with respect to longitudinal axis L7. It will be appreciated that transition area 784 is formed to permit both the bottom surface of connection portion 780 and the first plane to be in substantial alignment with the implant plane of plate 710. The extension member is locked in position by applying a nut 790 to the threaded post 754. It will be appreciated that nut 790 inhibits movement of the extension plate 780 in the direction of longitudinal axis L6 while the interdigitating engagement of splines 752 with the corresponding splines 786 on the bottom of connection portion 782 inhibits rotation of plate 780 about axis L6. Thus, the embodiment of FIGS. 7A and 7B provides a multi-axial connection between implant 710 and extension member 780.

Figure 8:
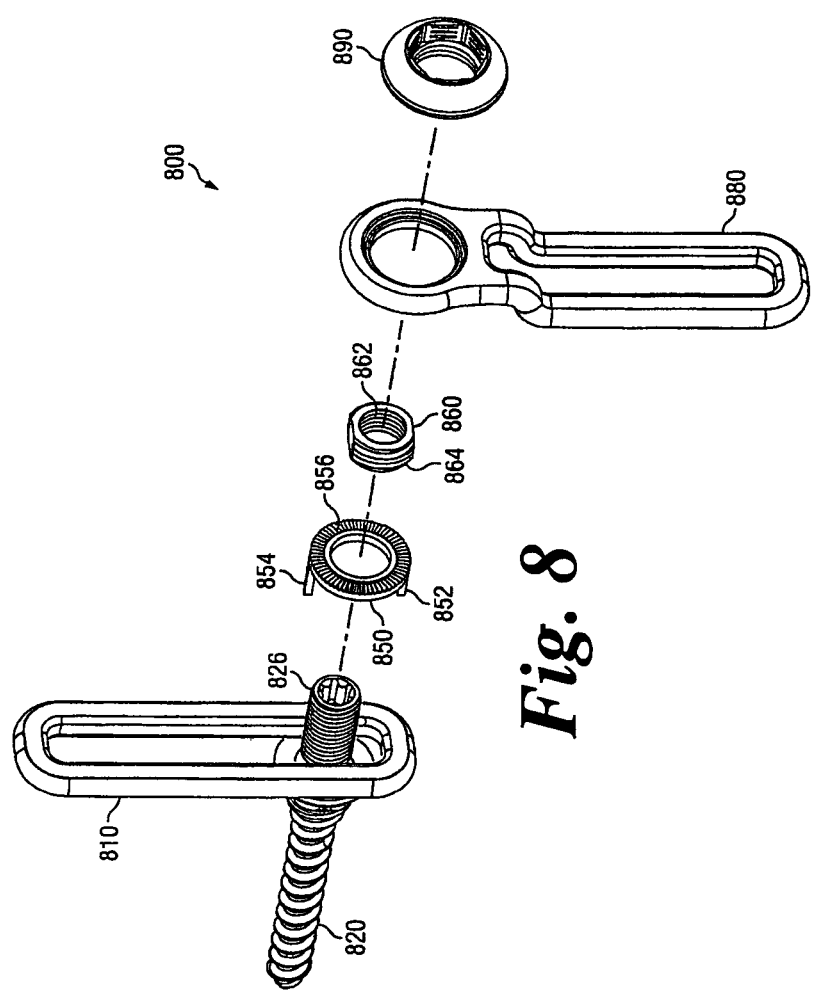
FIG. 8 is a partially exploded perspective view of a further embodiment of a fixation system.

Referring now to FIG. 8, there is shown still a further embodiment of a fixation system 800 according to another aspect of the present invention. Plate 810 represents a previously implanted fixation system attached to the bone via bone screw 820 having a post 826 with a series of external machine threads. A locking washer 850 includes a series of radially extending splines 856 projecting upwardly and a pair of downwardly projecting tabs 852 and 854. Locking washer 850 is positioned over threaded post 826 with tabs 852 and 854 extending into the slot of plate 810. A dual threaded nut 860 is advanced along threaded post 826 to engage a recessed area of washer 850 adjacent to the splines 856 to thereby lock the washer 850 to plate 810. Internal threads 862 engage the external threads of post 826. In one form, nut 860 includes a plurality of threads 864 to engage plate 880. Extension plate 880 has a series of radially extending splines corresponding to splines 856 formed on its bottom surface surrounding the mating aperture. The plate 880 is positioned over the threaded post 826 such that the splines on the bottom of the plate are matingly interdigitated with the splines 856. A locking nut 890 is applied to the threaded post 826 to lock the assembly in position. It will be appreciated that with the multi-angle coupling between the splines, plate 880 may extend at a plurality of angles with respect to plate 810. While tabs 852 and 854 are shown in the illustrated embodiment to resist rotation about the bone screw, it will be appreciated in an alternative embodiment the tabs are removed and resistance to rotation of the washer against the plate is accomplished by other forms such as compression onto the plate, a roughened surface on the washer bottom, frictional engagement or an interference fit.

Figure 9:
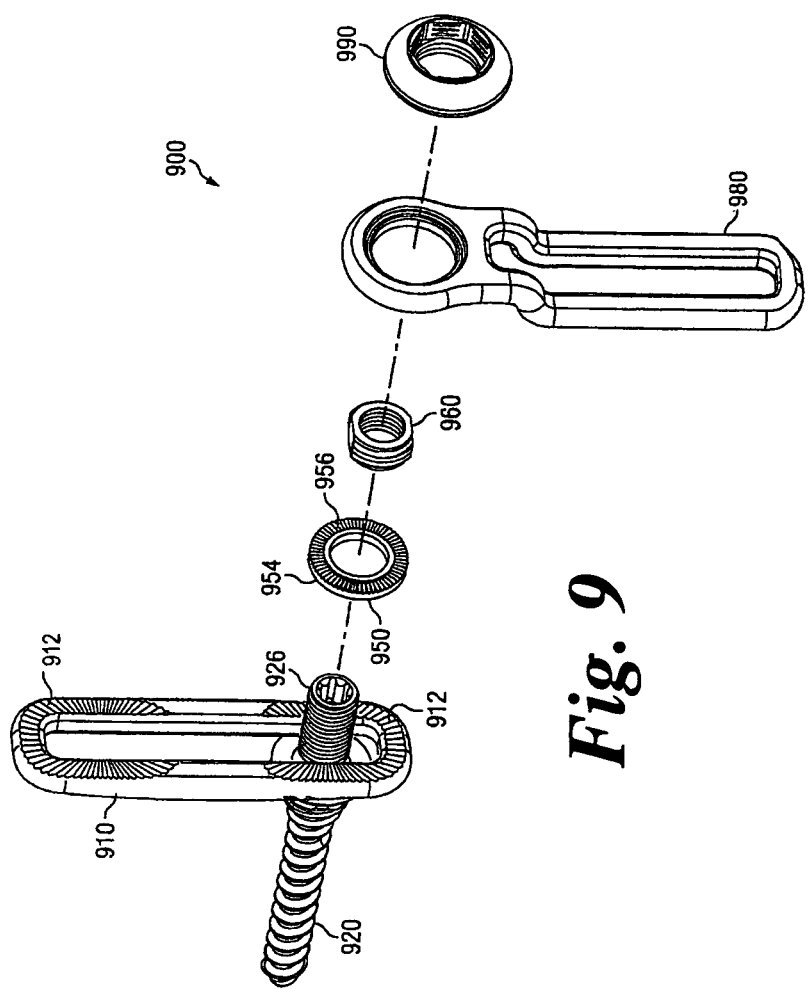
FIG. 9 is a partially exploded perspective view of a further embodiment of a fixation system.

Referring now to FIG. 9, there is shown yet a further embodiment of a fixation system 900 according to another aspect of the present invention. Plate 910 represents a previously implanted fixation system attached to the bone via bone screw 920 having a post 926 with a series of external machine threads. The upper surface of plate 910 is provided with a plurality of upwardly projecting splines 912. A locking washer 950 includes a series of radially extending splines 956 projecting upwardly and a series of downwardly projecting splines 954 configured to matingly engage splines 912. Locking washer 950 is advanced over threaded post 926 with the downwardly projecting splines extending into engagement with splines 912. A dual threaded nut 960 is advanced along threaded post 926 to engage a recessed area of washer 950 adjacent to the splines 956 to thereby lock the washer 950 to plate 910. Extension plate 980 has a series of radially extending splines corresponding to splines 956 formed on its bottom surface surrounding the mating aperture. The plate 980 is positioned over the threaded post 926 such that the splines on the bottom of the plate are matingly interdigitated with the splines 956. A locking nut 990 is applied to the threaded post 926 to lock the assembly in position. In an alternative embodiment, radially projecting splines are replaced with a series of ridges extending transverse to the longitudinal axis of the plate or with a knurled surface. The bottom of the washer, or the extension plate itself, is formed with a mating series of ridges or knurled surface.

Figure 10:
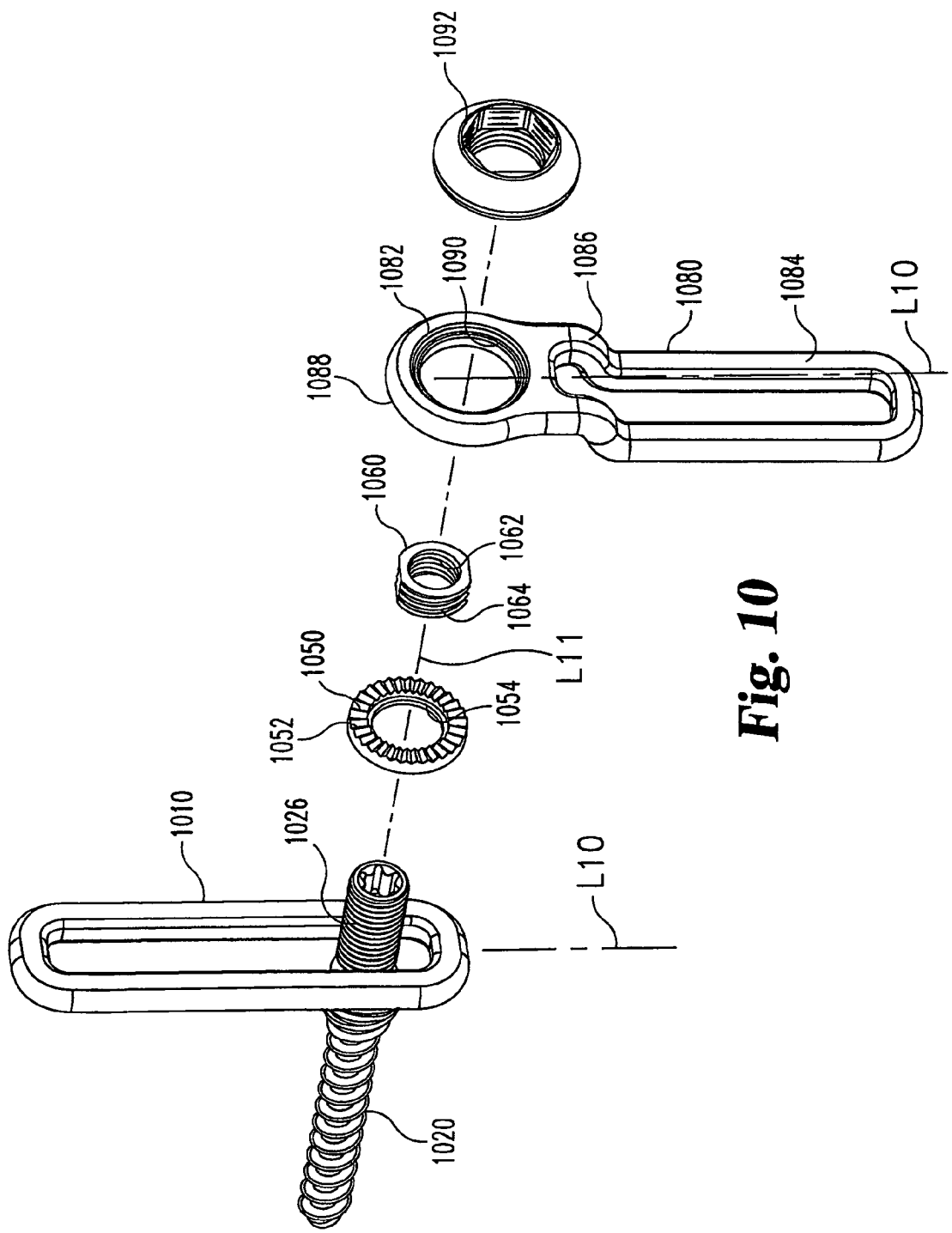
FIG. 10 is a partially exploded perspective view of a further embodiment of a fixation system.

Referring to FIG. 10, there is shown still another embodiment of the present invention. Plate 1010 represents a previously implanted fixation system attached to the bone with a bone screw 1020 having a post 1026 with a series of external machine threads. Plate 1010 extends along a longitudinal axis L10 with an upper surface extending substantially along an implant plane and bone screw 1020 extending along an axis L11 substantially transverse to axis L10. A locking washer 1050 includes a series of radially extending splines 1052 projecting upwardly. Locking washer 1050 also includes a recessed inner ring 1054. A dual threaded nut 1060 is advanced along threaded post 1026 to engage recessed inner ring 1054 of washer 1050 adjacent to the splines 1052 to lock the washer 1050 to plate 1010. Internal threads 1062 of nut 1060 engage the external threads of post 1026. Nut 1060 includes a plurality of threads 1064 to engage an elongated extension member 1080 as described below. While the compression connection between the plate 1010 and washer 1050 resists rotation about the bone screw, it will be appreciated in an alternative embodiment the resistance to rotation of the washer against the plate is accomplished by other forms such as interfitting splines on the plate and washer, a roughened surface on the washer bottom, frictional engagement, an interference fit or any combination thereof.

As shown in FIG. 10, a flexible elongated extension member 1080 is provided extending along longitudinal axis L10. As illustrated, extension member 1080 is a slotted plate having a coupling end portion 1082 opposite a bone engagement end portion 1084. Extending between coupling end portion 1082 and bone engagement end portion 1084 is a profile reduction transition area 1086 sloping between a first plane containing coupling end portion 1082 and a second plane containing bone engagement end portion 1084. In this embodiment, on the bottom of coupling end portion 1082 is a series of radially extending splines 1088 substantially identical to splines 1052 in size and arrangement such that splines 1088 may mate with splines 1052. Although an interconnection between the splines 1052 and splines 1088 is illustrated, it is contemplated that other forms of connections are possible to resist rotation of extension member 1080 about washer 1050. Some examples include frictional engagement, one or more slots and corresponding tongues or tabs, and/or roughened surfaces on the washer and coupling end portion. Coupling end portion 1082 defines an aperture 1090. In the illustrated embodiment, aperture 1090 is threaded to mate with external threads of a bone engagement fastener 1092, as described below.

Although illustrated at a substantially right angle to each other between plate 1010 and flexible elongated extension member 1080, extension member 1080 can be positioned at a plurality of angular relations with respect to plate 1010. Profile reduction transition area 1086 can be formed to permit both the bottom surface of coupling end portion 1082 and the first plane to be in substantial alignment with the implant plane of plate 1010. Extension member 1080 is locked in position by applying bone engagement fastener 1092 to threaded post 1026. In the illustrated embodiment, bone engagement fastener 1092 is a threaded nut 1090. In this form, bone engagement fastener 1092 inhibits movement of plate 1010 in the direction of longitudinal axis L11 while the interdigitating engagement of splines 1052 with the corresponding splines 1088 inhibits rotation of plate 1010 about axis L11.

In particular, extension member 1080 is made of any biocompatible material that will allow extension member 1080 to perform in a flexible manner. In one embodiment, extension member 1080 is made of polyetheretherketone or polyketone. In other embodiments, extension member 1080 is made of plastic, polymer, metals, or composites. In one embodiment, the flexibility of extension member 1080 provides a dynamic relationship between an existing spinal implant, such as plate 1010, and at least one additional vertebra in which extension member 1080 is connected or attached. Moreover, this dynamic relationship can optionally allow movement of the vertebrae in which plate 1010 and extension member 1080 are attached. This movement of the vertebrae allows the medical patient more flexibility and mobility of his spine as compared to traditional implants that may be formed of stiff or rigid material which restrict movement of the vertebrae. Optionally, this dynamic relationship can improve the overall mobility of the medical patient with an existing spinal implant and extension member 1080 as fewer vertebrae are rigidly held in place by a stiff, traditional implant system.

Figure 11:
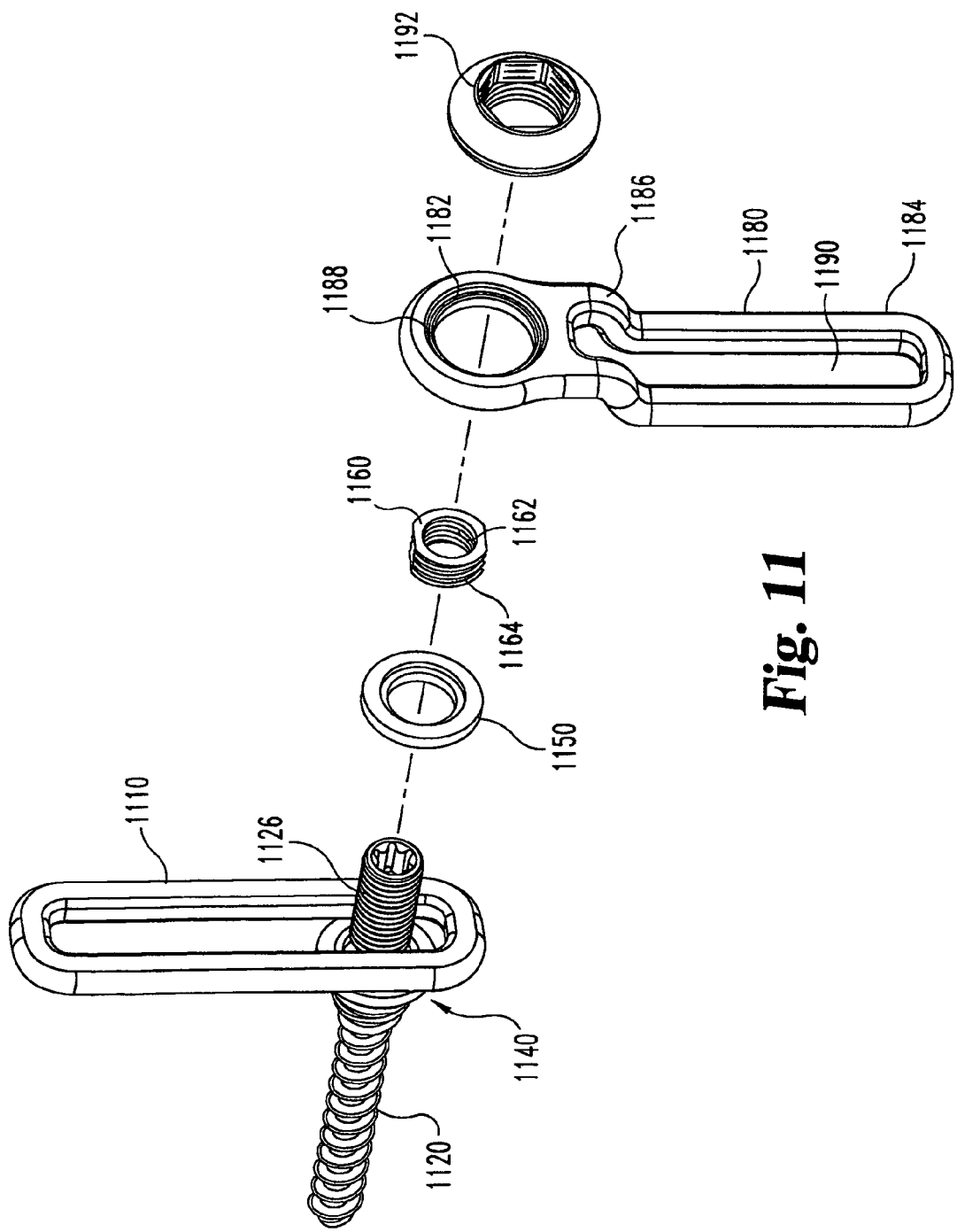
FIG. 11 is a partially exploded perspective view of another embodiment of a fixation system.

Referring to FIG. 11, there is shown another embodiment of previously implanted fixation system attachable to a system for extending the previously implanted fixation system to one or more additional vertebra. Plate 1110 is similar to plate 1010 and represents a previously implanted fixation system attached to the bone with a bone screw 1120 having a post 1126 with a series of external machine threads. In other embodiments, bone screw 1120 could be another form of fastener. For example, bone screw 1120 could be a hook, a rod, or any other fastener that can attach to bone. A first flexible coupler 1140 is positioned between plate 1110 and bone screw 1120. A second flexible coupler 1150 is positioned between plate 1110 and a dual threaded nut 1160. Nut 1160 is similar to nut 1060 as described above. Nut 1160 includes a plurality of internal threads 1162 and a plurality of external threads 1164.

Also shown in FIG. 11 is an elongated extension member 1180. In this embodiment, extension member 1180 is a slotted plate having a coupling end portion 1182 opposite a bone engagement portion 1184. Extension member 1180 also includes a profile reduction transition area 1186 sloping between coupling end portion 1182 and bone engagement portion 1184. Coupling end portion 1182 defines an aperture 1188. As shown, aperture 1188 includes a series of threads for mating with external threads of a bone engagement fastener 1192 as described below. Bone engagement portion 1184 defines a slot 1190. Slot 1190 has a substantially rectangular shape. Extension member 1180 is locked in position by applying a bone engagement fastener 1192 to threaded post 1126. As shown, bone engagement fastener 1192 is a threaded nut configured to mate with aperture 1188.

In particular, first flexible coupler 1140 and second flexible coupler 1150 are made of any biocompatible material that allows first flexible coupler 1140 and second flexible coupler 1150 to deform. For example, first flexible coupler 1140 and second flexible coupler 1150 can be made of silicone, plastic, polymer, metal, or composites. In one embodiment, the flexibility and/or compressibility of first flexible coupler 1140 and second flexible coupler 1150 provides a dynamic relationship between an existing spinal implant, such as plate 1110, and at least one additional vertebra in which extension member 1180 is connected or attached. In another embodiment, the flexibility of first flexible coupler 1140 and second flexible coupler 1150 provides a dynamic relationship between an existing spinal implant, such as plate 1110, and extension member 1180. Moreover, this dynamic relationship between existing spinal implant and extension member 1180 can allow movement of extension member 1180. This movement of extension member 1180 enables some movement of the vertebrae in which extension member 1180 is attached. Movement of vertebrae allows the medical patient more flexibility and mobility of his spine as compared to traditional implants that may be formed of stiff or rigid material that restrict movement of the vertebrae.

In other embodiments, elongated extension member 1180 can be configured differently. For example, in one embodiment, coupling end portion 1182 and bone engagement portion 1184 are substantially in the same plane without profile reduction transition area 1186. In another embodiment, slot 1190 may be shaped differently such as circular, oval, or trapezoidal. Additionally, in other embodiments slot 1190 may include one or more openings with a rib between each pair of openings. In these embodiments, the openings may be similarly shaped or have different shapes.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

The extension systems described above are formed of any suitable biocompatible material. It is contemplated that the extension system is formed of substantially the same material as the previously implanted fixation system. Examples of suitable materials include, but are provided without limitation to the use of alternative materials to form extension systems, metals such as stainless steel and titanium, composites, ceramics, plastics, and polymers. Further, while the illustrated embodiments have shown a number of components integrally formed with the elongated fixation member or plate, it is contemplated that such components may be separately formed and joined by any suitable connection.

Although the previously implanted system has been described for the purposes of illustration as a plate and pedicle screw system, it is contemplated that the present invention may be used with rod and screw systems, other plate and screw systems, and any spinal fixation or stabilization system to which the extension systems of the present disclosure may be connected.

It is understood that all spatial references, such as "top," "inner," "outer," "bottom," "left," "right," "anterior," "posterior," "superior," "inferior," "medial," "lateral," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A system for extending a first, implanted spinal fixation element to one or more additional adjacent vertebrae while leaving the first, implanted spinal fixation element in place, the system comprising:
   a flexible elongated extension member having a longitudinal axis extending between a coupling end portion and a bone engagement end portion, said flexible elongated extension member having a slot being defined by opposed elongated side walls and end walls, the extension member defining a length between said coupling end portion and said bone engagement portion wherein, when implanted, said flexible elongated extension member extends from said first, implanted spinal fixation element to the one or more additional vertebra;
   a projecting flange extending from the coupling end portion transverse to the longitudinal axis, the projecting flange is configured to align and fix the flexible elongated extension with the implanted spinal fixation element;
   a first fastener to position said coupling end portion on said first, implanted spinal fixation element; and
   a second fastener locking said coupling end portion to said first fastener.

2. The system of claim 1, wherein said elongated extension member is made of polyetheretherketone or polyketone.

3. The system of claim 1, wherein said elongated extension member is made of plastic.

4. The system of claim 1, wherein said flexible elongated extension member is configured to provide a dynamic relationship between said first, implanted spinal fixation element and said at least one additional vertebra.

5. The system of claim 1, further comprising a washer configured to position said coupling end portion on said first, implanted spinal fixation element.

6. A system for extending a first, implanted spinal fixation element having a plate, a first flexible coupler and a bone fastener attached to one or more additional vertebrae while leaving the bone fastener in place, the system comprising:
   an elongated extension member having a longitudinal axis extending between a coupling end portion and a bone engagement end portion, said elongated extension member having a slot being defined by opposed elongated side walls and end walls, the extension member defining a length between said coupling end portion and said bone engagement portion wherein, when implanted, said elongated extension member extends from said first, implanted spinal fixation element to the one or more additional vertebra, the elongated extension including a profile reduction transition area disposed between the coupling end portion and the slot and configured to align the implanted spinal fixation element and the elongated extension member;
   a first fastener to position said coupling end portion on said first, implanted spinal fixation element; and a second flexible coupler positioned between said coupling end portion and said first, implanted spinal fixation element.

7. The system of claim 6, wherein said second flexible coupler is made of silicone.

8. The system of claim 6, wherein said first flexible coupler is made of plastic.

9. The system of claim 6, wherein said first fastener is a dual threaded nut.

10. The system of claim 6, wherein said first flexible coupler and said second flexible coupler are configured to provide a dynamic relationship between said first, implanted spinal fixation element and said one or more vertebra.

11. The system of claim 6, wherein said first flexible coupler and said second flexible coupler are configured to provide a dynamic relationship between said first, implanted spinal fixation element and said elongated extension member.

12. A system for extending a first, implanted spinal fixation element to one or more additional adjacent vertebrae while leaving the first, implanted spinal fixation element in place, the system comprising:
- a flexible elongated extension member having a longitudinal axis extending between a coupling end portion and a bone engagement end portion, the elongated extension member defining a length and a slot between said coupling end portion and said bone engagement portion wherein, when implanted, said elongated extension member extends from said first, implanted spinal fixation element to the one or more additional vertebra;
- a projecting flange extending from the coupling end portion transverse to the longitudinal axis, the projecting flange is configured to align and fix the flexible elongated extension with the implanted spinal fixation element;
- a first fastener to position said coupling end portion on said first, implanted spinal fixation element; and
- a second fastener locking said coupling end portion to said first fastener.

13. The system of claim 12, wherein the projecting flange comprises a first projecting flange and further comprises a second projecting flange.

14. The system of claim 13, wherein the first and second projecting flanges define a channel, the channel receiving a plate of the first, implanted spinal fixation element.

\* \* \* \* \*